(12) United States Patent
Trumble

(10) Patent No.: US 6,945,926 B2
(45) Date of Patent: Sep. 20, 2005

(54) MUSCLE ENERGY CONVERTER

(75) Inventor: Dennis R. Trumble, Pittsburgh, PA (US)

(73) Assignee: Allegheny-Singer Research Institute, Pittsburgh, PA (US)

( * ) Notice: Subject to any disclaimer, the term of this patent is extended or adjusted under 35 U.S.C. 154(b) by 51 days.

(21) Appl. No.: 09/982,666

(22) Filed: Oct. 18, 2001

(65) Prior Publication Data

US 2003/0078464 A1 Apr. 24, 2003

(51) Int. Cl.[7] .............................................. A61M 1/12
(52) U.S. Cl. ....................................................... 600/16
(58) Field of Search ............................. 600/16, 17, 18; 623/321–323, 3.12, 3.27, 3.3; 128/899; 92/34, 36, 40, 44, 43, 47, 48, 163, 140, 127; 417/47.6, 229, 234, 395; 74/89, 110, 55

(56) References Cited

U.S. PATENT DOCUMENTS

| | | | | |
|---|---|---|---|---|
| 1,771,907 A | * | 7/1930 | Abramson | 417/569 |
| 1,814,632 A | * | 7/1931 | Rohr | 29/243.54 |
| 1,905,047 A | * | 4/1933 | Norin | 74/110 |
| 2,082,334 A | * | 6/1937 | Harcourt | 74/110 |
| 2,467,020 A | * | 4/1949 | Fischer | 74/110 |
| 3,073,246 A | * | 1/1963 | Saunders et al. | 417/389 |
| 3,513,486 A | * | 5/1970 | Cotton De Bennetot et al. | 623/3.18 |
| 4,134,306 A | * | 1/1979 | Grotness et al. | 74/29 |
| 4,185,617 A | * | 1/1980 | Hutchins | 600/16 |
| 4,277,706 A | * | 7/1981 | Isaacson | 310/80 |
| 4,541,788 A | * | 9/1985 | Nomura et al. | 417/471 |
| 4,966,067 A | * | 10/1990 | Ames et al. | 92/150 |
| 5,314,469 A | * | 5/1994 | Gao | 623/3.18 |
| 5,443,504 A | * | 8/1995 | Hill | 623/3.12 |
| 5,456,715 A | * | 10/1995 | Liotta | 623/3.12 |
| 5,479,946 A | * | 1/1996 | Trumble | 128/899 |
| 5,980,448 A | * | 11/1999 | Heilman et al. | 600/16 |

* cited by examiner

Primary Examiner—Jeffrey R. Jastrzab
(74) Attorney, Agent, or Firm—Ansel M. Schwartz

(57) ABSTRACT

A muscle energy converter for a patient. The converter includes a casing having a fluid port. The converter includes a bellows mechanism disposed in the casing adapted to contain fluid. The converter includes an actuator arm mechanism adapted to be attached to a tendon of a muscle of the patient which moves against the bellows mechanism when the muscle pulls the actuator arm mechanism and forces fluid out the fluid port. The actuator arm mechanism is engaged with the casing. A method for moving fluid in a patient with a muscle of a patient. The method includes the steps of rotating an actuator arm mechanism against a bellows mechanism in a casing when the muscle pulls the actuator arm mechanism. There is the step of forcing fluid out a fluid port of the casing as the actuator arm mechanism moves against the bellows mechanism.

11 Claims, 5 Drawing Sheets

DEVICE SHOWN AT FULL ACTUATOR ARM
ROTATION AND BELLOWS COMPRESSION

MUSCLE ENERGY CONVERTER

FIELD OF THE INVENTION

The present invention is related to a muscle energy converter. More specifically, the present invention is related to a muscle energy converter with a linear or rotary cam actuator.

BACKGROUND OF THE INVENTION

The purpose of the muscle energy converter (MEC) is to efficiently convert the power of linear muscle contractions into a form which can be used by a variety of implanted hydraulic actuators, including ventricular assist devices. The objective is to eliminate the need for external power supplies which contribute significantly to infection and device failures.

Considerable progress has been made over the last 30 years toward the development of implantable circulatory assist devices, but some fundamental problems still remain. No device in existence can provide both the reliability and unobtrusiveness required of a chronic implantable blood pump due, in large part, to the lack of a suitable power source. Current systems employ external power supplies with energy transmitted across the skin via tubes, wires, or electromagnetic fields. These schemes work well for short-term applications, but are not well-suited for chronic use due to infection and mechanical failure. However, many of these problems would be eliminated if a simple, implantable energy source could be developed.

Research on a device designed to perform the same function as the MEC device described herein is currently ongoing at California Pacific Medical Center (see Reichenbach S. H., K. J. Gustafson, G. D. Egrie, J. R. Weidman, D. J. Farrar, and J. D. Hill. Evaluation of a skeletal muscle energy convertor in a chronic animal model. *ASAIO J.* 46:482–485, 2000). There are however, substantial differences in design between these two technologies which render them quite distinct. These important distinctions are evidenced by the separate US patents issued to ASRI on 2, Jan. 1996 (U.S. Pat. No. 5,479,946) and CPMC on 22 Aug. 1995 (U.S. Pat. No. 5,443,504).

Based on results from $3^{rd}$-generation muscle energy converter (MEC3) bench testing and initial implant trials, significant design changes have been implemented to improve both function and biocompatibility of this device. Potential drawbacks of the MEC3 design scheme were found to be the following: low bellows durability; high bellows volumetric compliance; high housing profile; exposed actuation head; and potential shaft sheathing porosity. The design modifications described herein are meant to achieve the following: a) improve bellows durability; b) reduce or eliminate bellows compliance; c) lower device profile; d) eliminate exposed piston head; and e) eliminate the need for flexible sheathing.

SUMMARY OF THE INVENTION

The present invention pertains to a muscle energy converter for a patient. The converter comprises a casing having a fluid port. The converter comprises a bellows disposed in the casing adapted to contain fluid. The converter comprises an actuator arm in sliding relationship with the casing, the actuator arm having an attachment zone adapted to attach to a tendon of a muscle of the patient. The converter comprises a spring loaded lipseal and bushing attached to the casing and engaged with the actuator arm, the actuator arm having an original position and a compressed position. The converter comprises a roller bearing/cam follower mechanism in contact with the bellows, the bellows disposed between the fluid port and the roller bearing/cam follower mechanism. The converter comprises a cam disposed on the actuator arm which moves against the roller bearing/cam follower mechanism when the actuator arm moves from the original position to the compressed position and compresses the bellows and forces fluid out the fluid port when the muscle pulls the actuator arm. The bearing guiding the actuator arm and the bellows restoring the actuator arm to the original position from the compressed position.

The present invention pertains to a muscle energy converter for a patient. The converter comprises a casing having a fluid port. The converter comprises a bellows mechanism disposed in the casing adapted to contain fluid. The converter comprises an actuator arm mechanism adapted to be attached to a tendon of a muscle of the patient which moves against the bellows mechanism when the muscle pulls the actuator arm mechanism and forces fluid out the fluid port. The actuator arm mechanism is engaged with the casing.

The present invention pertains to a method for moving fluid in a patient with a muscle of a patient. The method comprises the steps of rotating an actuator arm mechanism against a bellows mechanism in a casing when the muscle pulls the actuator arm mechanism. There is the step of forcing fluid out a fluid port of the casing as the actuator arm mechanism moves against the bellows mechanism.

BRIEF DESCRIPTION OF THE DRAWINGS

In the accompanying drawings, the preferred embodiment of the invention and preferred methods of practicing the invention are illustrated in which.

DETAILED DESCRIPTION

Figure 1A:
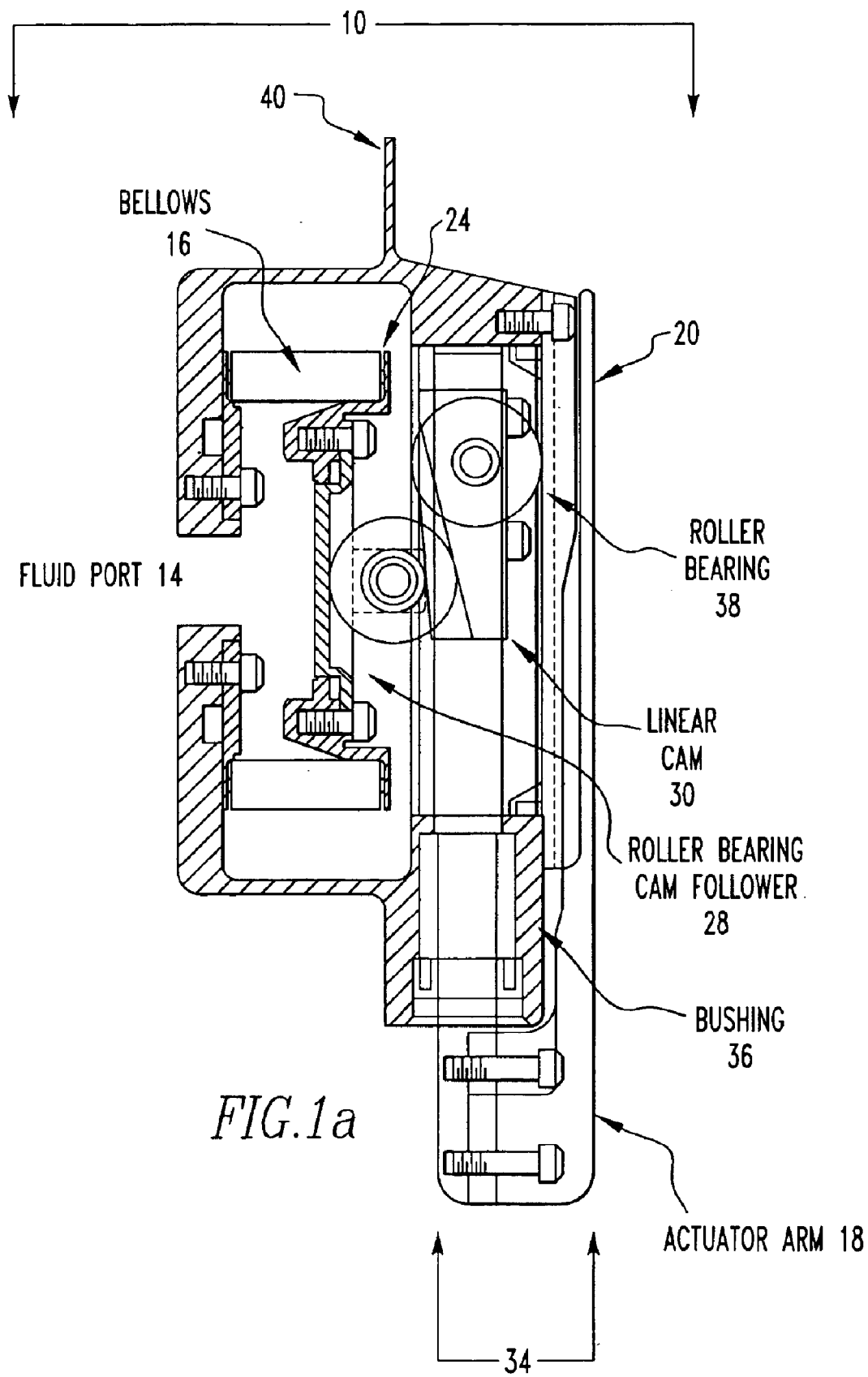
FIGS. 1a–1d are schematic representations of a muscle energy converter with a linear cam actuator.
Figure 1B:
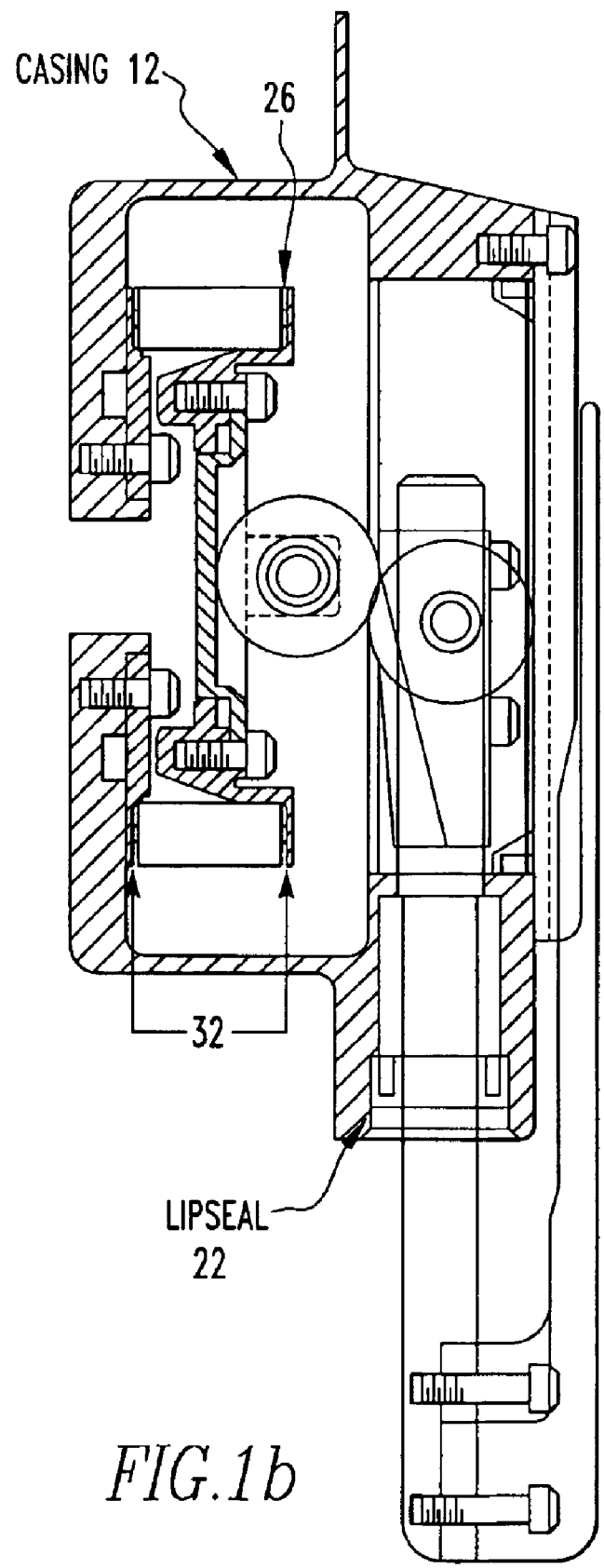
Figure 1C:
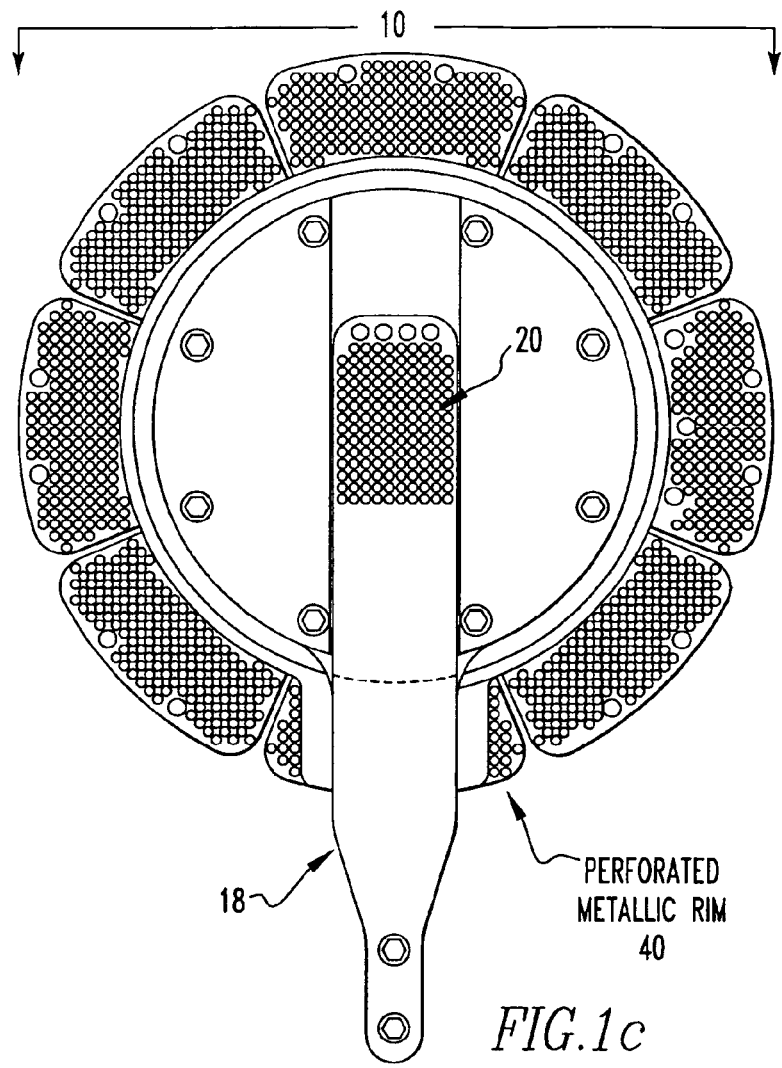
Figure 1D:
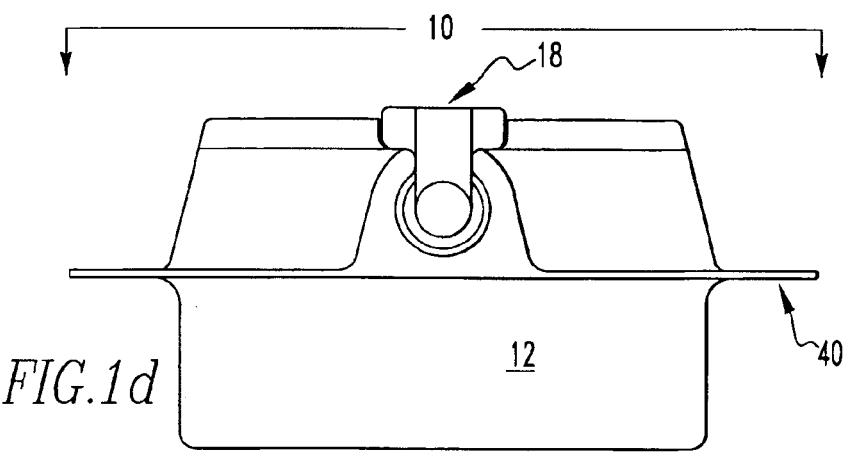

Referring now to the drawings wherein like reference numerals refer to similar or identical parts throughout the several views, and more specifically to FIGS. 1a–1d thereof, there is shown a muscle energy converter 10 for a patient. The converter 10 comprises a casing 12 having a fluid port 14. The converter 10 comprises a bellows mechanism 32 disposed in the casing 12 adapted to contain fluid. The converter 10 comprises an actuator arm mechanism 34 adapted to be attached to a tendon of a muscle of the patient which moves against the bellows mechanism 32 when the muscle pulls the actuator arm mechanism 34 and forces fluid out the fluid port 14. The actuator arm mechanism 34 is engaged with the casing 12.

Preferably, the actuator arm mechanism 34 has an actuator arm 18, the actuator arm 18 having an attachment zone 20 adapted to attach to a tendon of a muscle of the patient. The actuator arm mechanism 34 preferably has a bushing mechanism 36 which engages with the actuator arm 18 and the casing 12, and guides the actuator arm 18. Preferably, the bushing mechanism includes a spring loaded lipseal 22 and a bushing 36, the spring loaded lipseal 22 and the bushing attached to the casing 12 and engaged with the actuator arm 18, the actuator arm 18 having an original position 24 and a compressed position 26, the bushing guiding the actuator arm 18 and restoring the actuator arm 18 to the original position 24 from the compressed position 26.

The bellows mechanism 32 preferably includes a bellows 16 disposed in the casing 12 adapted to contain fluid. Preferably, the bellows mechanism 32 includes a roller bearing/cam follower mechanism 28 in contact with the bellows 16, the bellows 16 disposed between the fluid port 14 and the roller bearing/cam follower mechanism 28. The actuator arm mechanism 34 preferably includes a cam 30 disposed on the actuator arm 18 which pushes against the roller bearing/cam follower mechanism 28 when the actuator arm 18 moves from the original position 24 to the compressed position 26 and compresses the bellows 16 and forces fluid out the fluid port 14 when the muscle pulls the actuator arm 18.

Alternatively, the bellows mechanism 32 includes a roller bearing/cam follower 28. The actuator arm mechanism 34 preferably then includes a rotary cam 30 which rotates against the roller bearing/cam follower 28 when the muscle pulls the actuator arm mechanism 34. Preferably, the actuator arm mechanism 34 then includes a plurality of bushings which supports the rotary cam 30.

The present invention pertains to a muscle energy converter 10 for a patient. The converter 10 comprises a casing 12 having a fluid port 14. The converter 10 comprises a bellows 16 disposed in the casing 12 adapted to contain fluid. The converter 10 comprises an actuator arm 18 in sliding relationship with the casing 12, the actuator arm 18 having an attachment zone 20 adapted to attach to a tendon of a muscle of the patient. The converter 10 comprises a spring loaded lipseal 22 and bushing 36 attached to the casing 12 and engaged with the actuator arm 18, the actuator arm 18 having an original position 24 and a compressed position 26. The converter 10 comprises a roller bearing/cam follower mechanism 28 in contact with the bellows 16, the bellows 16 disposed between the fluid port 14 and the roller bearing/cam follower mechanism 28. The converter 10 comprises a cam 30 disposed on the actuator arm 18 which moves against the roller bearing/cam follower mechanism 28 when the actuator arm 18 moves from the original position 24 to the compressed position 26 and compresses the bellows 16 and forces fluid out the fluid port 14 when the muscle pulls the actuator arm 18. The bushing 36 guiding the actuator arm 18 and the bellows 16 restoring the actuator arm 18 to the original position 24 from the compressed position 26.

The present invention pertains to a method for moving fluid in a patient with a muscle of a patient. The method comprises the steps of rotating an actuator arm mechanism 34 against a bellows mechanism 32 in a casing 12 when the muscle pulls the actuator arm mechanism 34. There is the step of forcing fluid out a fluid port 14 of the casing 12 as the actuator arm mechanism 34 moves against the bellows mechanism 32.

Preferably, the moving step includes the step of moving a cam 30 of the actuator arm mechanism 34 against a roller bearing/cam follower 28 of the bellows mechanism 32. The forcing step preferably includes the step of forcing fluid out the fluid port 14 as the cam 30 moves against the roller bearing/cam follower 28.

Alternatively, the moving step includes the step of rotating a rotary cam 30 of the actuator arm mechanism 34 against a roller bearing/cam follower 28. The forcing step then includes the step of forcing fluid out the fluid port 14 as the rotary cam 30 rotates against the roller bearing/cam follower 28.

In the operation of the invention, the muscle energy converter (MEC) 10 represents a significant departure from previous related devices. In contrast, the MEC employs a circular casing 12 designed to house a pancake-shaped bellows 16 actuated by a linear or rotary cam 30 mechanism. Referring to FIGS. 1a–1d, the MEC features a large-diameter bellows 16 oriented so that its end fittings lie parallel to the plane of the chest wall. The fixed end attaches directly to the bottom (chest wall side) of the MEC housing and is centered over a fluid port 14 which passes directly into the thoracic cavity between the patient's ribs. The opposite (free) end of the bellows 16 is welded to a fixture supporting a dual roller bearing/cam follower mechanism 28 which rests beneath a linear cam 30 mounted on a sliding shaft. This shaft is supported by a linear bushing 36 and roller bearing 38 which serves as a low-friction guide. The shaft exits the housing through a spring-loaded lipseal 22 and terminates with a sintered anchor pad 20 for LD tendon attachment (shown as small circles on the actuator arm 18 in FIG. 1c). The device is actuated when the muscle pulls the shaft/cam 30 complex across the roller bearing such that the free end of the bellows 16 is pushed toward the fixed end, thereby ejecting fluid under pressure through the outlet port. Maximum shaft displacement is fixed at 16 mm. Bellows 16 stroke length and travel profile, on the other hand, are determined by the shape of the cam 30.

The costal side of the device is designed to pass through a window in the chest wall made by resection of 1–2 ribs. This feature is implemented to further lower the profile of the pump and improve device stability. Moreover, a thin rim of perforated metal extending about ½" from the device periphery is added to secure the housing to the chest wall, (this rim being segmented and thin enough to bend by hand so the surgeon can adjust the contour as needed).

Unlike edge-welded metallic bellows 16 used in prior MEC applications, the MEC bellows 16 has a relatively large effective radius (2.05 cm) compared to its expanded height (1.47 cm). This allows fluid to be pumped from inside the bellows 16 without causing the stacked convolutions to "squirm" toward one side—a phenomenon which can severely limit cycle life. Bellows of this shape also have the important advantages of extreme durability and low volumetric compliance. Moreover, because fluid is pumped from within the bellows 16, it can be cycled in compression while simultaneously providing a return force to reset the pump between contractions. This avoids having to maintain a resting fluid pressure in order to overcome the bellows' 16 spring rate and extend the piston arm. Design specifications call for a maximum bellows 16 stroke length of 0.38 cm (5 mL stroke volume) and a pressure capacity of 27.5 N/cm$^2$ (40 psi) in order transmit up to 1.37 joules per stroke cycle.

Because the MEC bellows 16 has been rotated 90 degrees from its orientation in prior designs, a mechanism is now required to redirect actuation forces perpendicular to axial shaft motion. A linear cam 30 attached to the shaft accomplishes this by acting as a simple inclined plane . . . as the shaft is drawn across the roller bearing, the free end of the bellows 16 is forced to move with the contours of the cam 30. This arrangement affords the added benefit that cam 30 profiles can be altered to compliment muscle function, (e.g., the leading edge can either be made steeper to allow the muscle to build force before shortening, or shallower to allow shortening at lower contractile forces).

A dual roller bearing is fixed to the free end of the metallic bellows 16 to provide a low-friction interface with the linear cam 30. This mechanism comprises a simple wheel-and-axle arrangement with two wheel bearings mounted on a single axle. Both ends of the axle are secured by a pair of mount blocks which flank the wheel bearings, (the axle being free to rotate within its moorings).

Body fluids are prevented from entering the device housing by a spring-loaded lipseal 22 which seals the actuation shaft. According to the manufacturer (American Variseal Corp., Hayward, Calif.) this collar seal provides: long wear; full chemical compatibility; very low friction; and extremely low leakage rates (tested using helium at high vacuum). Should this seal prove to be an effective fluid barrier under chronic implant conditions, it would eliminate the need to seal the shaft/housing interface using a flexible sheath (which must be made long enough to compress and extend 16 mm axially with minimal wear). This arrangement also reduces the risk of tissue adhesion along the "exposed" shaft length since: a) only a short length of highly polished shaft surface (<16 mm) is exposed to body fluids; and b) most of that length is cleansed with each actuation cycle as it passes through the seal).

The MEC actuation shaft is guided along its long axis by a linear bushing 36 stationed just inside the lipseal 22. A roller bearing 38 is placed on the shaft 18 at the level of the linear cam 30 in order to provide a low-friction means to support the cam 30 under load. The housing cover will ultimately support the load placed on the roller bearing as it rolls back-and-forth across its inner surface.

Fixation to the chest wall will be achieved using a thin, perforated metallic rim 40 extending roughly ½" from the mid-section of the device. This approach is analogous to the base-plate method successfully employed in prior device implants where scar tissue was observed to infiltrate and encapsulate the metal plating, anchoring the device in place. Because the MEC anchor plate spans the entire circumference of the device, the rim must be separated into several sections and made thin enough so that its contour may be altered at implant to accommodate variations in individual chest wall shape.

Contractile energy is transmitted from the MEC through a circular port centered beneath the bellows 16 and directed perpendicular to the chest wall. Port inner diameter may range from ⅛" to ⅞" and its profile altered according to need. The target device may attach directly to the MEC outlet port or be connected by flexible tubing to allow placement anywhere within the thoracic cavity.

Figure 2A:
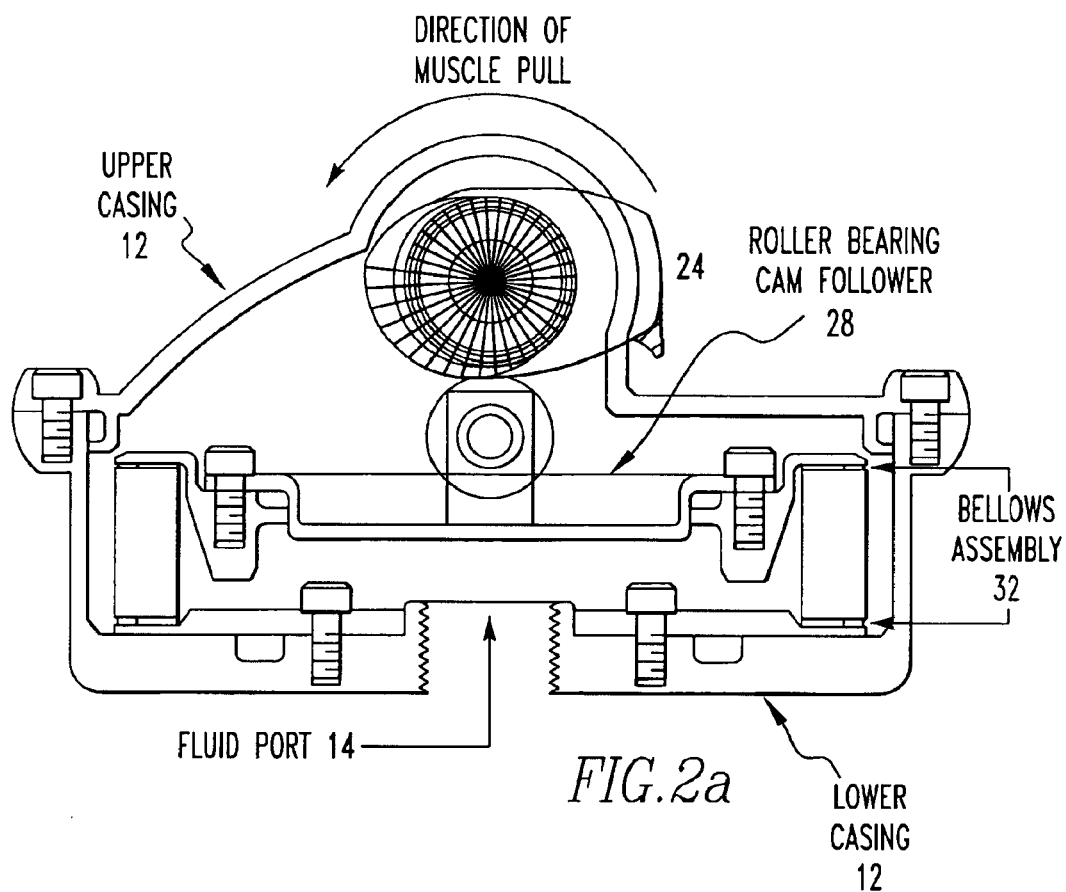
FIGS. 2a–2d are schematic representations of a muscle energy converter with a rotary cam actuator.
Figure 2B:
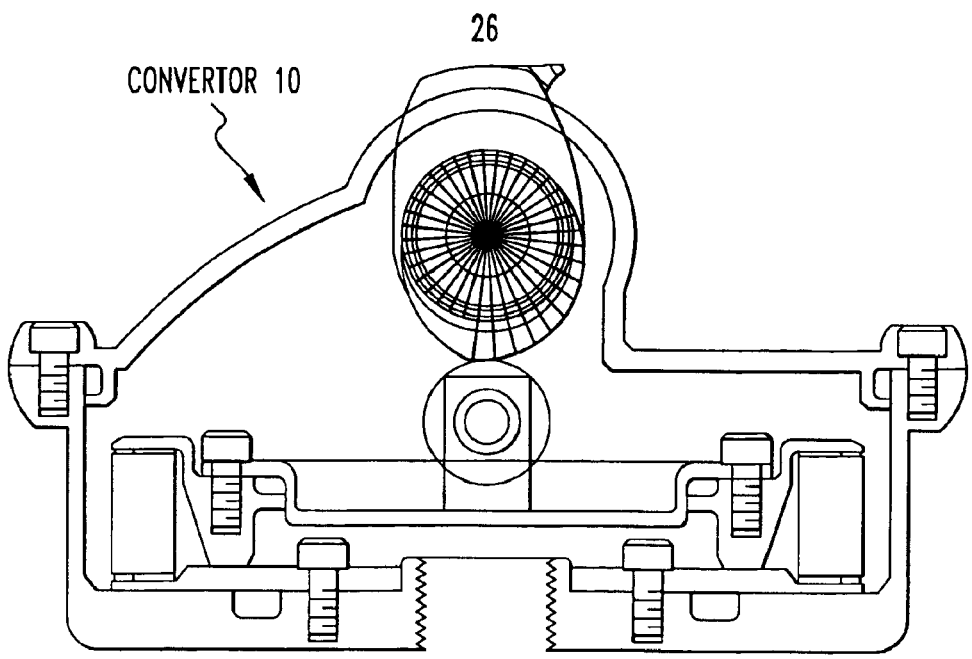
Figure 2C:
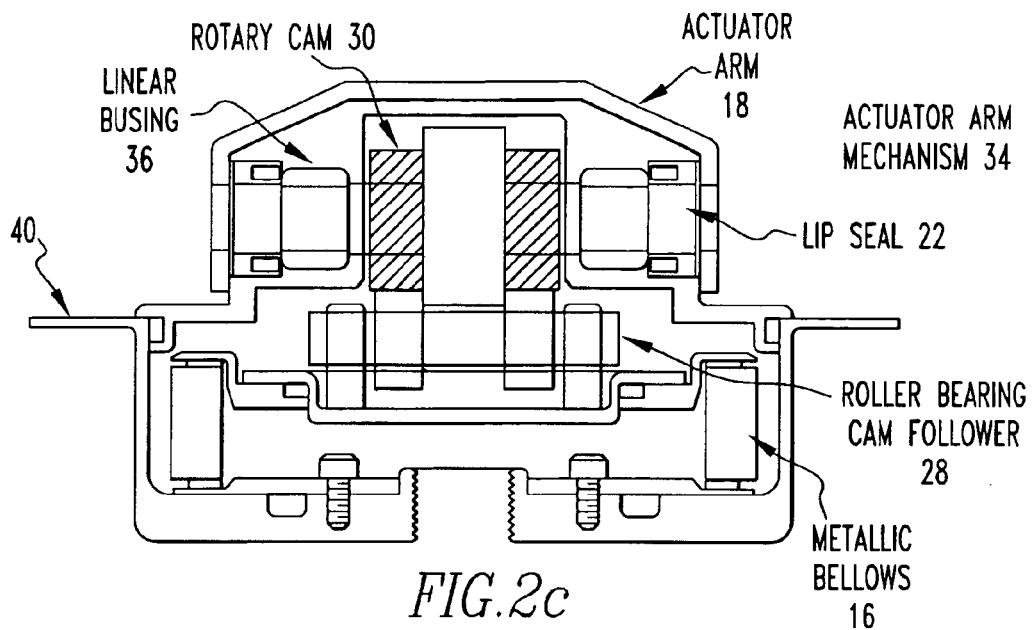
Figure 2D:
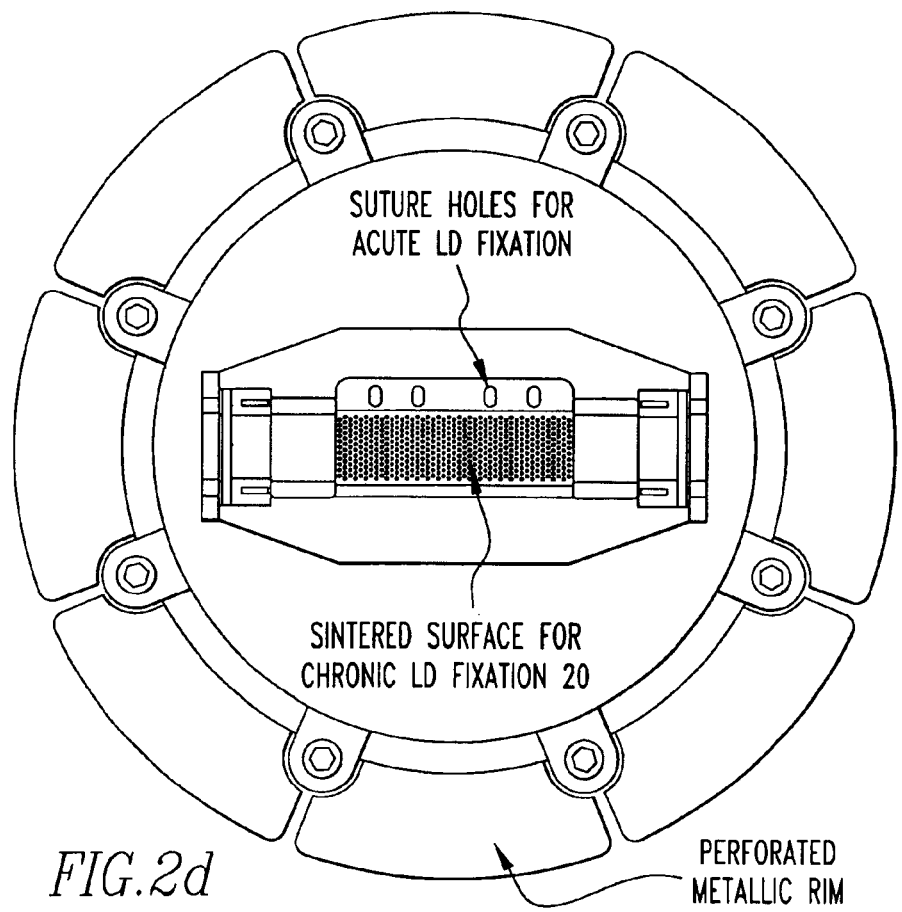

Bellows 16 compression may also be accomplished via a rotary cam 30 mechanism whereby the central shaft is rotated rather than displaced by the muscle. In this scheme, illustrated in FIGS. 2a–2d, a pair of bushings 36 is used to support the cam 30 shaft as it rotates about its long axis. The shaft passes through the upper housing via two spring-loaded lipseals 22 (described above) and connects to a rocker-arm 18 which spans the diameter of the device 12. The muscle tendon is sutured to the center portion of the actuation arm 20 to achieve short-term fixation; permanent fixation is achieved when the muscle tendon is allowed to grow into the porous sintered surface 20 of the rocker arm 18. Cam 30 profiles and rotation angles may be altered to optimize device performance—this embodiment allows the shaft to rotate 90 degrees while effecting a bellows 16 compression length of 0.38 cm. The principal advantages of this embodiment are: 1) there is less friction at the lipseal surfaces, resulting in a lower likelihood of seal failure, and 2) there is no reciprocation arm that travels away from the upper housing, making it less likely that binding will occur as a result of tissue encumbrance.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A muscle energy converter for a patient comprising:
   a casing having a fluid port;
   a bellows disposed in the casing adapted to contain fluid;
   an actuator arm in sliding relationship with the casing, the actuator arm having an attachment zone adapted to attach to a tendon of a muscle of the patient;
   a bushing and spring loaded lipseal attached to the casing and engaged with the actuator arm, the actuator arm having an original position and a compressed position;
   a roller bearing/cam follower mechanism in contact with the bellows, the bellows disposed between the fluid port and the roller bearing/cam follower mechanism; and
   a cam disposed on the actuator arm which moves against the roller bearing/cam follower mechanism when the actuator arm moves from the original position to the compressed position and compresses the bellows and forces fluid out the fluid port when the muscle pulls the actuator arm, the bearing guiding the actuator arm and the bellows restoring the actuator arm to the original position from the compressed position.

2. A muscle energy converter for a patient comprising:
   a casing having a fluid port;
   a bellows mechanism disposed in the casing adapted to contain fluid; and
   an actuator arm mechanism adapted to be attached to a tendon of a muscle of the patient which moves against the bellows mechanism when the muscle pulls the actuator arm mechanism and forces fluid out the fluid port, the actuator arm mechanism engaged with the casing, the actuator arm mechanism has an actuator arm, the actuator arm having an attachment zone adapted to attach to a tendon of a muscle of the patient, the actuator arm mechanism has a bushing mechanism which engages with the actuator arm and the casing, and guides the actuator arm.

3. A converter as described in claim 2 wherein the bushing mechanism includes a spring loaded lipseal and a bushing, the spring loaded lipseal and the bushing attached to the casing and engaged with the actuator arm, the actuator arm having an original position and a compressed position, the bushing guiding the actuator arm and the bellows restoring the actuator arm to the original position from the compressed position.

4. A converter as described in claim 3 wherein the bellows mechanism includes a bellows disposed in the casing adapted to contain fluid.

5. A converter as described in claim 4 wherein the bellows mechanism includes a roller bearing/cam follower mechanism in contact with the bellows, the bellows disposed between the fluid port and the roller bearing/cam follower mechanism.

6. A converter as described in claim 5 wherein the actuator arm mechanism includes a cam disposed on the actuator arm which pushes against the roller bearing/cam follower mechanism when the actuator arm moves from the original position to the compressed position and compresses the bellows and forces fluid out the fluid port when the muscle pulls the actuator arm.

7. A converter as described in claim 2 wherein the actuator arm mechanism includes a plurality of bushings which supports the rotary cam.

8. A method for moving fluid in a patient with a muscle of a patient comprising the steps of:

rotating an actuator arm mechanism against a bellows mechanism in a casing when the muscle pulls the actuator arm mechanism, including the step of moving a cam of the actuator arm mechanism against a roller bearing/cam follower of the bellows mechanism; and forcing fluid out a fluid port of the casing as the actuator arm mechanism moves against the bellows mechanism.

9. A method as described in claim 8 wherein the forcing step includes the step of forcing fluid out the fluid port as the cam moves against the roller bearing/cam follower.

10. A method for moving fluid in a patient with a muscle of a patient comprising the steps of:

rotating an actuator arm mechanism against a bellows mechanism in a casing when the muscle pulls the actuator arm mechanism, including the step of rotating a rotary cam of the actuator arm mechanism against a roller bearing cam follower; and forcing fluid out a fluid port of the casing as the actuator arm mechanism moves against the bellows mechanism.

11. A muscle energy converter for a patient comprising:

a casing having a fluid port;

a bellows mechanism disposed in the casing adapted to contain fluid, the bellows mechanism includes a roller bearing cam follower; and an actuator arm mechanism adapted to be attached to a tendon of a muscle of the patient which moves against the bellows mechanism when the muscle pulls the actuator arm mechanism and forces fluid out the fluid port, the actuator arm mechanism engaged with the casing has an actuator arm, the actuator arm having an attachment zone adapted to attach to a tendon of the actuator arm mechanism includes a rotary cam which rotates against the roller bearing cam follower when the muscle pulls the actuator arm mechanism.

* * * * *